United States Patent [19]

Solomon

[11] 4,311,668
[45] Jan. 19, 1982

[54] MICRO CLEANUP AND CONCENTRATION APPARATUS FOR TRACE RESIDUE ANALYSIS BY GAS LIQUID CHROMATOGRAPHY

[76] Inventor: John Solomon, 29 Waterford Bay, Winnipeg, Manitoba, Canada, R3T 1H6

[21] Appl. No.: 182,017

[22] Filed: Aug. 28, 1980

[51] Int. Cl.³ .............................................. G01N 31/08
[52] U.S. Cl. .................................. 422/70; 73/61.1 C; 210/198.2; 422/89; 422/99
[58] Field of Search ..................... 422/70, 89, 99, 100, 422/101, 103; 73/61.1 C, 422 GC; 210/656, 198.2; 55/386

[56] References Cited

U.S. PATENT DOCUMENTS

| | | | |
|---|---|---|---|
| 2,378,949 | 6/1945 | Post | 422/101 X |
| 3,010,800 | 11/1961 | Whitehead et al. | 422/70 |
| 3,449,083 | 6/1969 | Pelick | 73/61.1 C X |
| 3,869,068 | 3/1975 | Chen | 422/100 |
| 4,012,200 | 3/1977 | Leeuw | 422/100 |
| 4,229,414 | 10/1980 | Stecher et al. | 422/101 |

OTHER PUBLICATIONS

Analytical Chemistry, vol. 51, pp. 1861-1863, Sep. 1979, Solomon.

*Primary Examiner*—Kenneth M. Schor
*Attorney, Agent, or Firm*—Stanley G. Ade

[57] ABSTRACT

The elongated glass filament used in the filament concentrator of a micro cleanup and concentration apparatus for trace residue analysis by gas liquid chromatography includes a jacket with an elongated filament freely suspended from a feed tube and terminating with a distal end situated adjacent the reduced drip tip of the jacket and being centralized thereby due to the inner wall of the flow tip being concentric with but slightly spaced from the outer surface of the distal end of the filament. A hypodermic needle assembly extends between the chromatographic column and the feed tube to meter the eluant through the hypodermic needle, which is readily changed depending upon the flow rate required.

20 Claims, 11 Drawing Figures

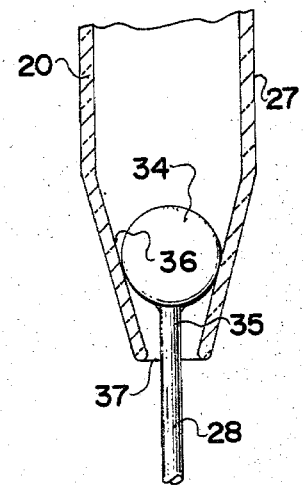
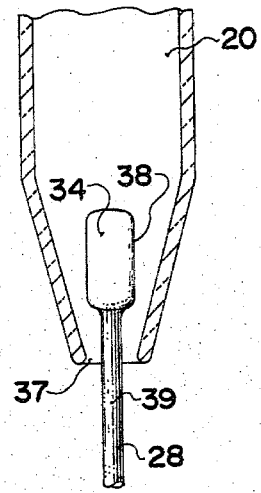
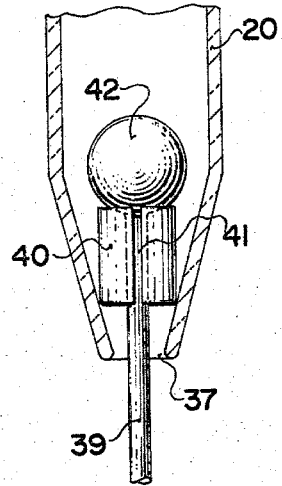
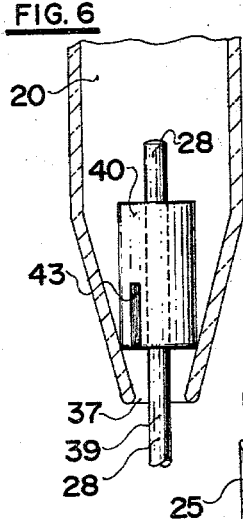
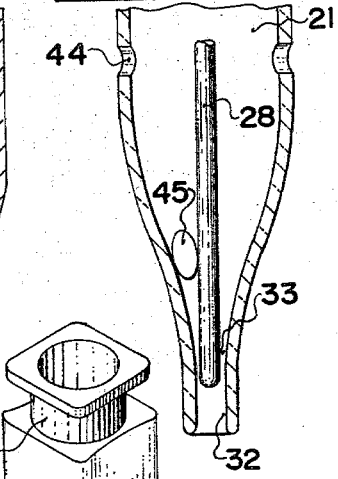
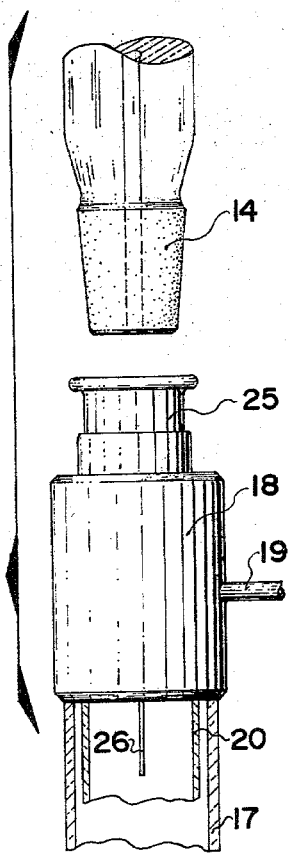
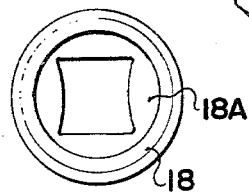
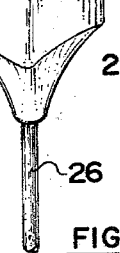

MICRO CLEANUP AND CONCENTRATION APPARATUS FOR TRACE RESIDUE ANALYSIS BY GAS LIQUID CHROMATOGRAPHY

BACKGROUND OF THE INVENTION

This invention relates to new and useful improvements in sample procedure preparations for the analysis of pesticides, toxic chemicals and drugs using micro techniques of column chromatographic cleanup and concentration as a one-step procedure. All previous methods required individual sample handling at the cleanup stage and individual concentration prior to gas liquid chromatography.

In toxicological studies of pesticides, for example, there is often a need to analyze large numbers of small tissue samples. Although rapid methods of extraction of small samples have been developed, the cleanup and concentration of the extract for gas chromatographic analysis is somewhat time consuming. Furthermore, the recommended multiresidue procedure for cleanup of extracts containing insecticides, other toxic chemicals and pollutants use relatively large quantities of chromatographic materials and solvents as well as requiring separate evaporation of the eluant and transfer to a test tube for gas chromatographic analysis.

There has been developed an apparatus for the micro cleanup and concentration of trace residue analysis by gas liquid chromatography and such apparatus is described in an article by the applicant and published in Analytical Chemistry Volume 51, page 1861, September 1979.

In the apparatus described therein, a glass filament concentrator is shown consisting of a cylindrical glass jacket and a glass filament therein. The glass filament is hand drawn from solid glass tubing and terminates in a one millimeter diameter glass filament of some thirty centimeters in length.

This filament is concentric with the inner wall of the jacket and not only is extremely difficult to produce commercially, but suffers from several disadvantages. Firstly, it vibrates due to inherent ambient vibration and occasionally a concentrated drop is lost on the joint resulting in large false lower readings. Breakage also occurs readily during transportation, handling and storage of such apparatus. Furthermore, if a last drop of liquid gathers at the lower tip of the filament, it tends to evaporate as the weight thereof is often not sufficient to enable it to drop and be collected. This also causes additional losses and hence false readings to the end result.

SUMMARY OF THE INVENTION

The present invention overcomes these disadvantages and in accordance with the invention there is provided, in a micro cleanup and concentration apparatus for trace residue analysis by gas liquid chromatography which includes a chromatographic column and a filament concentrator operatively connected thereto; the improvement comprising in combination an elongated, substantially vertically situated cylindrical jacket, an elongated substantially vertical filament concentrator therein, means freely suspending said elongated filament concentrator within said jacket and means adjacent the lower end of said jacket to centralize and stabilize the distal end of said elongated filament concentrator.

Another advantage of the present invention is the use of a hypodermic needle as the metering device between the chromatographic collar and the filament concentrator. Such hypodermic needles are available commercially in standard precision gauges thus enabling the rate of feed of the eluant to be controlled depending upon the test circumstances, it being understood that such hypodermic needles are readily available and readily exchanged within the apparatus.

Another advantage of the present invention is to provide a device of the character herewithin described in which the elongated, relatively narrow diameter filament is easily formed either from glass or stainless steel and which is centred and stabilized at the lower end thereof and suspended freely from a restricted end of a feed tube situated at the upper end of the jacket so that manufacture is facilitated and the losses due to vibration are eliminated. The whole apparatus is less fragile and repair of a broken filament is now made possible to replace.

A still further advantage of the invention is to provide a device of the character herewithin described which is simple in construction, economical in manufacture and otherwise well suited to the purpose for which it is designed. The new design has been field tested and compares well with other macro methods.

With the foregoing in view, and other advantages as will become apparent to those skilled in the art to which this invention relates as this specification proceeds, the invention is herein described by reference to the accompanying drawings forming a part hereof, which includes a description of the preferred typical embodiment of the principles of the present invention, in which:

DESCRIPTION OF THE DRAWINGS

FIG. 3 is an enlarged fragmentary cross sectional view of one embodiment showing the suspension of the filament within the lower end of the feed tube.

FIG. 4 is a side view of FIG. 3.

FIG. 5 is a view similar to FIG. 3, but showing the preferred embodiment.

FIG. 6 is a further embodiment of the upper end of the filament within the lower restricted end of the feed tube.

FIG. 7 is an enlarged fragmentary cross sectional view of the distal or lower end of the filament within the drip tip of the jacket.

FIGS. 8–10 provide enlarged views of portions of FIGS. 2 and 2A.

In the drawings like characters of reference indicate corresponding parts in the different figures.

DETAILED DESCRIPTION

Figure 1:
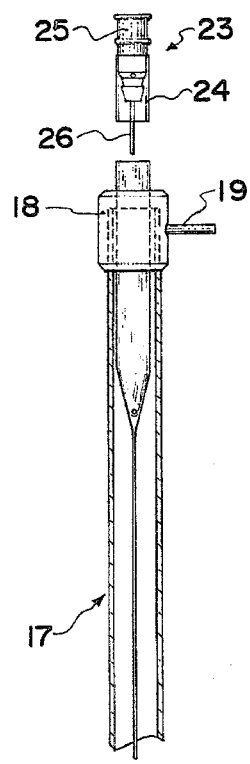
FIG. 1 is a schematic side elevation of the filament concentrator in which the glass filament is formed integrally from a solid glass rod, and which constitutes prior art.
Figure 2A:
FIG. 2 is a partially schematic side elevation of the assembly including the chromatographic column and the filament concentrator of the present invention, the upper part of FIG. 2, which upper part is designated as FIG. 2A, being in side by side relationship with the lower part thereof.
Figure 2A:
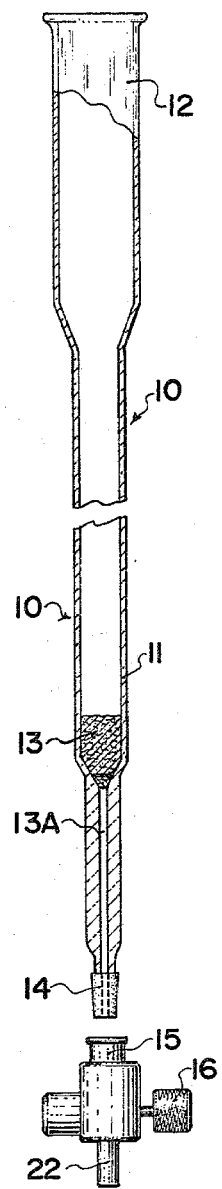

Proceeding therefore to describe the invention in detail, reference should be made to FIGS. 1 and 2A which show prior art devices and in which reference characters 17 and 10 represent the concentrator and column respectively. The column is self-supported in a half-hazard vertical alignment on top of the concentrator, by the teflon-butt connection 24. The teflon tubing is permanently heat sealed to the hypodermic needle component 25 and is an individual permanent assembly, making direct hypodermic needle replacement for flow control adjustment or damaged, difficult in the field. The concentrator 17 is normally held in a support (not illustrated) and is operatively connected to a source of metered helium via the inlet 19, said helium acting as an evaporating gas for the solvent such as hexane contained within the eluant. However, such apparatus is fully described in Analytical Chemistry Volume 51, page 1861, September 1979 and it is therefore not believed necessary to describe same further.

Figure 2:
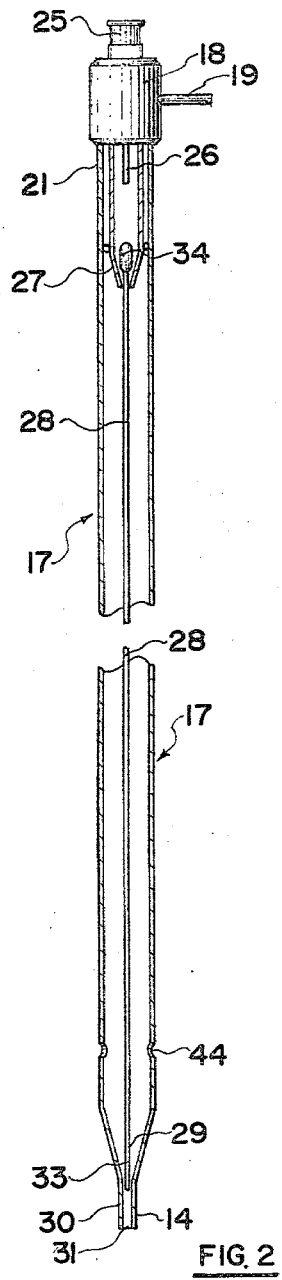

The new design consists of concentrator 17 shown in FIG. 2 and a column similar to that shown in FIG. 2A. The column includes a cylindrical tube 11 with a reservoir portion 12 at the upper end thereof, a fibre filter 13 adjacent the lower end thereof, and a Luer taper connection on the lower end thereof which may be engaged within a stopcock component 16. The stopcock component 16 is provided with a Luer fitting 15 on the upper end thereof and a Luer taper 22 on the lower end thereof (obtainable commercially as a separate item).

The column 10 is self-supported on the concentrator 17 in perfect vertical alignment by the Luer taper engaging within the upper end 25 of a hypodermic needle assembly situated in the upper end of the cylindrical tube 17.

A cylindrical or tubular fitting 18 is engaged around the upper end of the tube 17 and a hypodermic needle component receptacle 18A is of the push-in/pull-out construction in a teflon molded construction inner sleeve for direct simple hypodermic needle replacement. A shaped aperture is formed in this receptacle corresponding to the shaped or square body portion 26A of the conventional hypodermic needle. This cylindrical sleeve 18 also includes the inlet tube 19 operatively connectable to a source of metered helium as hereinbefore described relative to the prior art. The push-in engagement of a standard hypodermic needle component such as that shown in FIG. 10, makes replacement or exchange simple, fast and inexpensive in the field. The design also makes it possible for more rigid self-support of the column. A relatively simple column mounting is essential as it has to be removed every 15 or 20 minutes to empty and replace the column packing in preparation for the next sample run.

The hypodermic needle 26 engages within a feed tube 20 also held by adhesive or the like within the cylindrical fitting 18.

The lower end 27 of the feed tube 20 is restricted due to the inwardly tapering cross sectional configuration thereof and of course the distal end of the feed tube is open.

The elongated filament 28 is formed from glass or stainless steel and is approximately one millimeter in diameter and means are provided at the upper end thereof to freely suspend the filament within the restricted lower end 27 so that it extends through the open end of the feed tube and is freely suspended within the cylindrical jacket 25.

The lower or distal end 29 of the filament 28 is stabilized by restricted means provided at the lower end of the jacket. In the present invention, the lower end of the jacket is in the form of a drip tip 30 inasmuch as the lower end tapers inwardly and terminates with the discharge tip exit 31 and the lower end 29 of the filament (see FIG. 7) is in concentric relationship with the inner wall 32 of the tip but is spaced slightly therefrom. This means that slight vibration can occur but this vibration is removed due to the restriction between the outer surface 33 of the filament and the inner wall 32 of the tip.

Various means are provided to suspend the filament within the restricted lower end 27 of the feed tube and reference should be made to FIGS. 3 to 6.

FIGS. 3 and 4 show a flattened ball 34 formed or otherwise secured to the upper end 35 of the filament. This ball rests upon the inner wall 36 of the restricted lower end 27 and suspends the filament through the lower open discharge 37 of the feed tube. The flattened sides 38 of the ball provide a liquid passage between the interior of the feed tube and the external surface 39 of the filament so that liquid can flow from the feed tube and down the outer surface of the filament.

FIG. 5 shows a cylindrical collar 40 frictionally engaged around the upper end of the filament and freely engaging and being supported by the inner walls 36 of the restricted lower end, once again concentrically supporting the filament through the discharge lower end 37 of the feed tube. In this embodiment, a vertical slit 41 is formed through the collar acting as a fluid passage between the interior of the feed tube and the outer wall 39 of the filament. If desired, a ball 42 can be provided or secured to the upper end of the filament above the collar 40.

FIG. 6 shows a still further embodiment in which the collar 40 relies on the frictional engagement with the filament 28 to prevent downward movement of the filament relative to the collar. In this embodiment, a relatively short slit 43 is provided within the wall of the collar to act as a fluid passageway as hereinbefore described.

In operation, the eluant is fed to the reservoir 12 of the chromatographic column and flows through the filter 13 and through a relatively fine feed tube 13A extending from the lower end of the filter through the Luer taper and into the connector 15. With the shut-off valve 16 in the open position, this eluant passes to the interior of the hypodermic needle assembly 25 and drips from the distal end of the needle 26, the rate being controlled by the diameter of the bore thereof. The eluant then flows slowly along the glass filament 28 to the discharge tip exit 31.

Metered helium enters through the inlet tube 19 and evaporates the solvent from the element to a desired concentration. Helium and solvent vapors escape through vent holes 44 formed in the jacket adjacent the lower end thereof and the sample concentrate collects in receiving tubes (not illustrated) situated below the drip tip.

Reference to FIG. 7 will show one of the advantages of the present construction as compared to the prior art construction.

In the prior art construction, occasional (additive) concentrate which are lost on the joint, are unrecovered, and will drastically lower the end result.

However, in the present device, all drops will engage the inner surface 32 of the drip tip and are all collected in the receiver indicated by reference character 45 in FIG. 7. Therefore, it runs down the surface of the drip tip into the receiving tube.

Since various modifications can be made in my invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

What I claim as my invention is:

1. In a micro cleanup and concentration apparatus for trace residue analysis by gas liquid chromatography which includes a liquid chromatographic column and a filament concentrator operatively connected thereto such that fluid from the column will be fed to the concentrator; the improvement wherein the concentrator comprises in combination an elongated, substantially vertically situated cylindrical jacket, an elongated substantially vertical filament located within said jacket, means for freely suspending said elongated filament within said jacket and means adjacent the lower end of said jacket for centralizing and stabilizing the distal lower end of said elongated filament.

2. The invention according to claim 1 in which said means for centralizing and stabilizing includes a restricted lower end portion on said jacket, the outer surface of said filament being closely situated but spaced from the inner surface of the wall of said restricted lower end portion.

3. The invention according to claim 2 in which said restricted lower end portion is in the form of a drip tip formed on the lower end of said jacket.

4. The invention according to claim 1 in which said means for freely suspending said filament includes a vertically situated feed tube secured to adjacent the upper end of said jacket, a restricted open lower end to said feed tube, and means on the upper end of said filament pivotally suspended within the restricted lower end of said feed tube, said last mentioned means including means to transfer liquid from the interior of the feed tube to the outer surface of said filament.

5. The invention according to claim 2 in which said means freely suspending said filament includes a vertically situated feed tube secured to adjacent the upper end of said jacket, a restricted open lower end to said feed tube, and means on the upper end of said filament pivotally suspended within the restricted lower end of said feed tube, said last mentioned means including means to transfer liquid from the interior of the feed tube to the outer surface of said filament.

6. The invention according to claim 3 in which said means freely suspending said filament includes a vertically situated feed tube secured to adjacent the upper end of said jacket, a restricted open lower end to said feed tube, and means on the upper end of said filament pivotally suspended within the restricted lower end of said feed tube, said last mentioned means including means to transfer liquid from the interior of the feed tube to the outer surface of said filament.

7. The invention according to claim 4 in which said means to transfer liquid from the interior of said feed tube to the outer surface of said filament includes a flattened ball formed on the upper end of said filament freely engaging within said restricted lower end of said feed tube and suspending said filament therefrom, said flattened ball forming fluid passageways between the sides of said flattened ball and the inner wall of said restricted lower end of said feed tube.

8. The invention according to claim 5 in which said means to transfer liquid from the interior of said feed tube to the outer surface of said filament includes a flattened ball formed on the upper end of said filament freely engaging within said restricted lower end of said feed tube and suspending said filament therefrom, said flattened ball forming fluid passageways between the sides of said flattened ball and the inner wall of said restricted lower end of said feed tube.

9. The invention according to claim 6 in which said means to transfer liquid from the interior of said feed tube to the outer surface of said filament includes a flattened ball formed on the upper end of said filament freely engaging within said restricted lower end of said feed tube and suspending said filament therefrom, said flattened ball forming fluid passageways between the sides of said flattened ball and the inner wall of said restricted lower end of said feed tube.

10. The invention according to claim 4 in which said means to transfer liquid from the interior of said feed tube to the outer surface of said filament includes a cylindrical collar frictionally engaged around the upper end of said filament freely engaging within said restricted lower end of said feed tube and suspending said filament therefrom, and a vertical slit formed in said collar forming a fluid passageway between said collar and the inner wall of said restricted lower end of said feed tube.

11. The invention according to claim 5 in which said means to transfer liquid from the interior of said feed tube to the outer surface of said filament includes a cylindrical collar frictionally engaged around the upper end of said filament freely engaging within said restricted lower end of said feed tube and suspending said filament therefrom, and a vertical slit formed in said collar forming a fluid passageway between said collar and the inner wall of said restricted lower end of said feed tube.

12. The invention according to claim 6 in which said means to transfer liquid from the interior of said feed tube to the outer surface of said filament includes a cylindrical collar frictionally engaged around the upper end of said filament freely engaging within said restricted lower end of said feed tube and suspending said filament therefrom, and a vertical slit formed in said collar forming a fluid passageway between said collar and the inner wall of said restricted lower end of said feed tube.

13. The invention according to claim 10 which includes means on the upper end of said filament above said collar to restrict downward movement of said filament through said collar.

14. The invention according to claim 11 which includes means on the upper end of said filament above said collar to restrict downward movement of said filament through said collar.

15. The invention according to claim 12 which includes means on the upper end of said filament above said collar to restrict downward movement of said filament through said collar.

16. The invention according to claims 1, 2 or 3 which includes means operatively connecting the lower end of said chromatographic column to the upper end of said jacket, said means including means to control the rate of flow of liquid from said column to said feed tube, said last mentioned means including a hypodermic needle engaging by the upper end thereof to the lower end of said column, the discharge end of said needle engaging within said feed tube, the diameter of the bore of said needle controlling the rate of discharge of fluid from said column to said feed tube.

17. The invention according to claims 4, 5 or 6 which includes means operatively connecting the lower end of said chromatographic column to the upper end of said jacket, said means including means to control the rate of flow of liquid from said column to said feed tube, said last mentioned means including a hypodermic needle engaging by the upper end thereof to the lower end of said column, the discharge end of said needle engaging within said feed tube, the diameter of the bore of said needle controlling the rate of discharge of fluid from said column to said feed tube.

18. The invention according to claims 7, 8 or 9 which includes means operatively connecting the lower end of said chromatographic column to the upper end of said jacket, said means including means to control the rate of flow of liquid from said column to said feed tube, said last mentioned means including a hypodermic needle engaging by the upper end thereof to the lower end of said column, the discharge end of said needle engaging within said feed tube, the diameter of the bore of said needle controlling the rate of discharge of fluid from said column to said feed tube.

19. The invention according to claims 10, 11 or 12 which includes means operatively connecting the lower end of said chromatographic column to the upper end of said jacket, said means including means to control the rate of flow of liquid from said column to said feed tube, said last mentioned means including a hypodermic needle engaging by the upper end thereof to the lower end of said column, the discharge end of said needle engaging within said feed tube, the diameter of the bore of said needle controlling the rate of discharge of fluid from said column to said feed tube.

20. The invention according to claims 13, 14 or 15 which includes means operatively connecting the lower end of said chromatographic column to the upper end of said jacket, said means including means to control the rate of flow of liquid from said column to said feed tube, said last mentioned means including a hypodermic needle engaging by the upper end thereof to the lower end of said column, the discharge end of said needle engaging within said feed tube, the diameter of the bore of said needle controlling the rate of discharge of fluid from said column to said feed tube.

* * * * *